(12) United States Patent
Freudenberger et al.

(10) Patent No.: US 7,187,753 B2
(45) Date of Patent: Mar. 6, 2007

(54) MONOCHROMATOR FOR AN X-RAY RADIATOR ALLOWING MODIFICATION OF THE X-RAY SPECTRAL COMPOSITION

(75) Inventors: Jörg Freudenberger, Baiersdorf (DE); Erich Hell, Gingen (DE); Peter Schardt, Höchstadt (DE)

(73) Assignee: Siemens Aktiengesellschaft, Munich (DE)

( * ) Notice: Subject to any disclaimer, the term of this patent is extended or adjusted under 35 U.S.C. 154(b) by 105 days.

(21) Appl. No.: 10/774,131

(22) Filed: Feb. 6, 2004

(65) Prior Publication Data
US 2004/0218718 A1 Nov. 4, 2004

(30) Foreign Application Priority Data
Feb. 6, 2003 (DE) ................. 103 04 852

(51) Int. Cl.
*G21K 1/06* (2006.01)
(52) U.S. Cl. ......................... 378/84; 378/115
(58) Field of Classification Search ................. 378/84, 378/115
See application file for complete search history.

(56) References Cited

U.S. PATENT DOCUMENTS

| | | | | |
|---|---|---|---|---|
| 3,806,726 A | * | 4/1974 | Ishijima ..................... 378/49 |
| 4,365,156 A | * | 12/1982 | Golovchenko et al. ....... 378/84 |
| 4,398,823 A | | 8/1983 | Brown et al. |
| 4,698,833 A | | 10/1987 | Keem et al. |
| 4,736,398 A | * | 4/1988 | Graeff et al. ............... 378/98.3 |
| 5,028,778 A | | 7/1991 | Ninomiya et al. |
| 5,268,954 A | * | 12/1993 | Middleton .................... 378/85 |
| 6,038,285 A | * | 3/2000 | Zhong et al. ................. 378/84 |
| 6,327,335 B1 | * | 12/2001 | Carroll ........................ 378/85 |
| 2005/0129169 A1 | * | 6/2005 | Donnelly et al. .............. 378/5 |

FOREIGN PATENT DOCUMENTS

| | | |
|---|---|---|
| DE | 196 06 913 | 8/1987 |
| DE | 41 27 778 | 11/1992 |
| DE | 199 45 773 | 4/2001 |
| EP | 0 924 967 | 6/1999 |

OTHER PUBLICATIONS

U.S. Statutory Invention Registratin H313.
"Über die Optimalisierung der Röntgenquantenenergie in der Röntgendiagnostik," Keller et al, Elektromedizin vol. 10 (1965) pp. 153-158.
"Theoretische Untersuchungen zur Optimierung der Quantenenergie in der Röntgendiagnostik," Freyer et al, Forschr. Röntgenstr., vol. 123 (1975) pp. 571-579.

(Continued)

*Primary Examiner*—Edward J. Glick
*Assistant Examiner*—Thomas R. Artman
(74) *Attorney, Agent, or Firm*—Schiff Hardin LLP

(57) ABSTRACT

A monochromator to be used in an X-ray device having an X-ray source is formed by a crystal for spectral restriction of X-rays produced by the X-ray source. The monochromator includes a positioning device that can move the crystal so that it changes the spectral composition of the X-radiation. The crystal can be moved so that it changes the angle between an X-ray path and the crystal, or so that the crystal is removed out of X-ray path or returned into it.

12 Claims, 1 Drawing Sheet

OTHER PUBLICATIONS

"Mosaic Crystal Monochromators For Synchrotron Radiation Instrumentation," Freund, Nuclear Instruments and Methods in Physics Research A266 (1988) pp. 461-466.

"Resolution Properties of a Large Area Quasi-monochromatic X-ray Source for Mammography," Gambaccini, SPIE, vol. 3336 (1998) pp. 65-75.

* cited by examiner

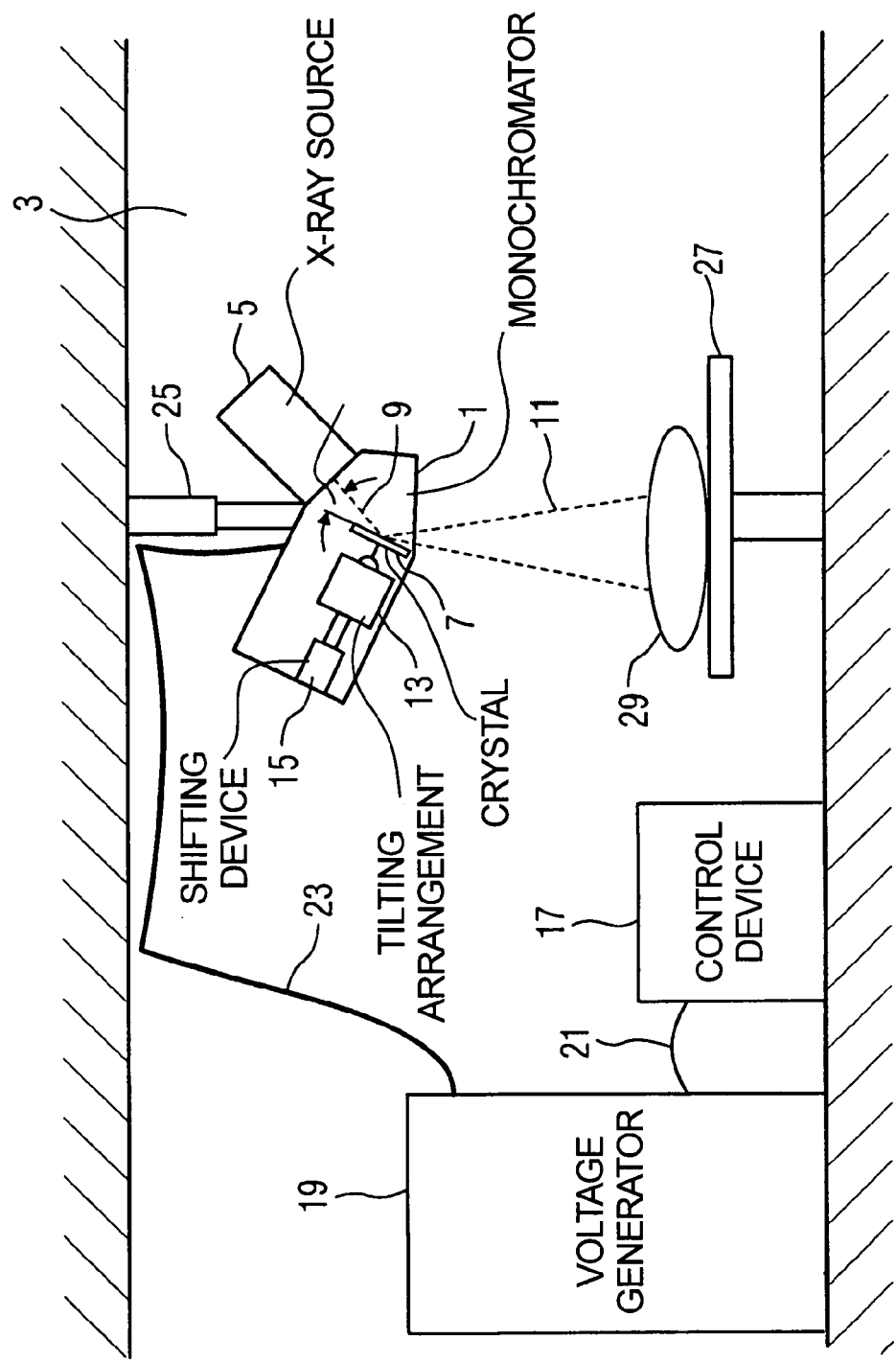

MONOCHROMATOR FOR AN X-RAY RADIATOR ALLOWING MODIFICATION OF THE X-RAY SPECTRAL COMPOSITION

BACKGROUND OF THE INVENTION

1. Field of the Invention

The present invention concerns a monochromator for an X-ray device of the type having an X-ray source with a crystal for spectral restriction of the X-ray produced by the X-ray source. The invention also concerns an X-ray device that incorporates such a monochromator.

2. Description of the Prior Art

X-rays are used in medical and technical diagnostics to obtain images of objects to be examined. The quality of images thus produced depends on the radiation dose and on the energy spectrum of the X-rays. In order to achieve a certain minimum image quality, a certain minimum radiation dose is required, and the minimum radiation dose itself depends on the spectral energy distribution in the X-rays. In addition, depending on the concrete body or object to be examined, there always exists an optimum level of X-radiation energy, i.e., the wavelength of the X-radiation at which a maximum contrast resolution with a simultaneous minimized radiation dose can be achieved. Thus, in order to achieve the requisite minimum image quality with a minimized radiation dose, X-radiation of a suitable spectrum must be used.

The spectral energy distribution of X-rays, however, can be influenced at the X-ray source only to a limited extent. For example, the energy spectrum of a conventional X-ray tube always contains wavelength components outside the wavelength that is optimal for the radiation dose and the contrast resolution. The energy spectrum of an X-ray tube is influenced by the choice of anode material and by the type of X-ray absorption filters used. Furthermore, the aforementioned energy spectrum also strongly depends on the X-ray voltage, i.e., the energy with which electrons inside the X-ray tube are accelerated from the cathode to the anode. The X-ray voltage determines the upper limit of the energy spectrum.

Changes in the X-ray voltage affect not only the energy spectrum, but also the radiation dose, because with decreasing X-ray voltage, the tube current, i.e., the electron flow inside the X-ray tube, decreases. Thus, in order to compensate for the reduction of the radiation dose with a decrease in X-ray voltage, the X-ray tube current must be increased. The increase of the X-ray tube current, however, is restricted by the so-called blooming effect, by which—due to a lower X-ray voltage and high X-ray currents—the X-ray focal spot on the anode of the X-ray tube enlarges. The blooming effect negatively affects the properties of the X-rays that are produced.

Currently, depending on the particular application, a suitable energy spectrum is achieved by an appropriate combination of the anode material, the X-ray absorption filters, and the X-ray voltage. Each energy spectrum thus is necessarily a compromise among the various parameters.

European Application 0 924 967 discloses an X-ray device with a monochromator designed on the basis of a so-called mosaic crystal. The mosaic crystal is arranged in the path of radiation beam in such a manner that the X-rays of the X-ray tube are reflected by it. On the basis of Bragg relation for the diffraction of X-rays, for a certain reflection direction spectrally restricted, i.e., quasi-monochromatized, X-rays are obtained. In order to obtain X-rays of various wavelengths, the aforementioned European application proposes to implement multiple mosaic crystals to provide various Bragg angles. The arrangement of multiple mosaic crystals and their associated diaphragms requires a number of components and is therefore costly. Moreover, this arrangement has the inherent drawback that different propagation paths are pre-determined for the X-rays, which have to be individually aimed at the particular object to be examined.

SUMMARY OF THE INVENTION

An object of the present invention is to provide a monochromator for an X-ray device that makes it possible to variably spectrally restrict X-rays produced by an X-ray device using a reflection crystal, with such a monochromator being inexpensive to design and easy to operate.

The above object is achieved in accordance with the present invention by a monochromator for an X-ray device that comprises an X-ray source with a crystal for spectral restriction of the X-ray produced by the X-ray source, wherein, according to the invention, the crystal can be adjusted by a positioning device so that the energy spectrum of the spectrally restricted X-radiation can be changed. The ability to adjust the crystal provides the possibility of adjusting the energy spectrum of the spectrally restricted X-radiation to comply with the requirements for the image to be acquired without having to set the X-ray voltage and X-ray tube current to non-optimal values. For example, using this design the blooming effect that occurs at low X-ray voltages and high X-ray currents can be avoided, or the X-ray tube can always be operated with an X-ray voltage suitable for the particular requisite level of efficiency. At the same time, the adjustability of the crystal allows for a variable adjustment of the energy spectrum to various requirements without the need for changes in the X-ray source (for example, in the anode material).

Consistent with conventionally-used terminology, the subject matter described herein is referred to as a "monochromator" even though it does not limit the X-ray radiation to a monochromatic (single energy) beam, but instead spectrally restricts the X-radiation.

In an embodiment of the invention, the crystal is adjustable so that the angle between the X-rays (produced by the X-ray source) and the crystal can be changed. According to the Bragg relation, the energy spectrum of the spectrally restricted X-radiation changes dependent on the change of the diffraction angle. Therefore, the ability to change the angle provides a simple and inexpensive means of producing X-radiation with variable energy spectra. Greater changes in the angle, which can be achieved, for example, by tilting the crystal, change the entire X-ray path. However, such changes can be simply compensated for, e.g., by a simultaneous tilting of the X-ray source. The tilting of the crystal performed together with a coordinated tilting of the X-ray source allows for a simple continuous variation of the energy spectrum of X-radiation with an unchanged X-ray path.

In another embodiment of the invention, the crystal can be adjusted so that it can be fully removed from and returned into the X-ray path produced by the X-ray source. If the crystal is removed from the X-ray path, Bragg diffraction of the X-ray is prevented, and the original energy spectrum of the X-ray source is reconstituted. Thus, the option of removing and then returning the crystal to the X-ray path provides a simple way of producing either spectrally restricted X-rays or X-rays without any spectral restriction. If, during the removal of the crystal, certain adjustments have to be made to reflect the change in the entire X-ray path, for example, by tilting the X-ray source, this is easy to do.

In another embodiment of the invention, the crystal can be automatically adjusted so that we reach a maximum value of the energy spectrum of the spectrally restricted X-radiation is reached that is between 0.34- and 0.8-multiples of the maximum value of the original (unrestricted) energy spectrum of the X-ray source. The original energy, which is greater than in the spectrally restricted X-radiation, is produced by an increased X-ray voltage, which means the blooming effect is reduced. At the same time, by maintaining a minimal factor of about 0.34, the influence of higher-order reflection in the energy spectrum of the spectrally restricted X-radiation is minimized. Higher-order reflection occurs at double, triple, quadruple, etc. the minimum value of the original X-radiation. The indicated range rules out the possibility that reflections from the 3rd order and beyond will be contained in the spectrally restricted X-radiation.

DESCRIPTION OF THE DRAWINGS

FIG. 1 shows an X-ray device with a monochromator in accordance with this invention.

DESCRIPTION OF THE PREFERRED EMBODIMENTS

The figure illustrates an X-ray device 3 with a monochromator 1 in accordance with the invention. The monochromator 1 is an accessory device that is connected to the X-ray source 5 as a module; however, the device can also be fully integrated with the X-ray sources. Other components of the X-ray tube, such as a diaphragm, are not essential to the explanation of the invention and therefore are not illustrated.

The X-ray device 3 produces spectrally restricted X-radiation 11 in order to generate an image of a patient 29 lying on a patient positioning table 27. Depending on the type of the required X-ray image, the X-ray path of X-radiation 11 can assume various orientations by moving and turning the X-ray source 5 mounted on the ceiling stand. This also allows examination of, for example, a standing patient, with the monochromator 1 always being used in the same manner.

A voltage generator 19, which is connected to the X-ray source 5 by an electrical line 23, generates the X-ray voltage and the X-ray tube current to operate the X-ray source 5. The X-ray generator 19 is controlled by a control device 17, which is connected to the X-ray generator 19 by a control line 21. The control device 17 allows entry of all the parameters of the X-ray image that is to be produced.

The basic component of the monochromator 1 is a crystal 7, which reflects X-rays propagating in an X-ray path 9. The reflection at the crystal spectrally restricted X-radiation 11, the energy spectrum of which depends on the angle of the reflection. The maximum value of the energy spectrum of the spectrally restricted X-radiation 11 follows from the Bragg relation as follows:

$$\sin\Theta = \frac{k \cdot \lambda}{2 \cdot a}$$

where $\Theta$ represents the angle between the X-ray path 9 and the crystal 7, k is a natural number and denotes the order of the reflection, I represents the wavelength of the maximum value of the energy spectrum of the spectrally restricted X-radiation 11, and a represents a property of the crystal lattice of the crystal 7.

Bragg reflection of the X-ray by crystals produces X-radiation at a relatively narrow peak in the energy spectrum for each reflection order k. While such a narrow energy spectrum can be advantageous for many applications, it presents the problem of a relatively low radiation dose. Therefore, a widening of the energy spectrum and thus a widening of its peak in the range of the maximum value must be accepted in order to reach an accordingly increased radiation dose. For this reason, a mosaic crystal is as the preferred type of the crystal 7 for medical X-ray devices. The preferred type of the crystal 7 is a mosaic crystal made of layers of highly oriented pyrolytic graphite (HOPG). The direction in space of the crystal lattice should vary around 1°.

Due to different lattice orientations of the crystal molecules or atoms represented by the factor a of the aforementioned Bragg's relation, mosaic crystals produce an energy spectrum that is widened very slightly. Spectrally restricted X-radiation with a peak widened in this manner will reach the radiation doses required in medical diagnostics.

The energy spectrum of the spectrally restricted X-radiation 11 can be changed by changing the angle of incidence $\Theta$ of the X-ray 9 on the crystal 7. For this purpose, the crystal 7 can be tilted using a positioning device that includes a tilting arrangement 13. However, this tilting changes not only the angle of incidence $\Theta$, but also the reflection angle. Because of this correspondent change, the ray path of the spectrally restricted X-radiation 11 changes too, so that its focus can shift. In the case of small changes in the angle of incidence $\Theta$ this effect plays only a minor role, but a substantial change of the angle can result in the focus leaving the intended (and targeted) zone of the patient 29 to be examined. This means that after larger changes occur in the energy spectrum due to the tilting of the crystal 7, the region to be examined must be targeted again. In order to avoid this problem, the crystal 7 can be tilted simultaneously with the X-ray source 5 or with the entire arrangement of the X-ray source 5 and the monochromator 1 so that this process compensates for any change in the ray path. Since, in order to be able to target any possible section of a patient 29 to be examined, the X-ray source 5 usually is arranged so that it can be fully moved in all directions in space, all that is required to compensate for a tilting movement of the crystal 7 is to perform a coordinated tilting of the X-ray source 5.

Since the crystal 7 and the X-ray source 5 must be movable in relation to each other only in one plane, in order to influence the angle $\Theta$, quite simple angle ratios are obtained. The simple angle ratios allow us to perform the compensation for the tilting movement of the crystal 7 either by an independent control of the tilting movement of the X-ray source 5, or by providing a mechanism for coupling the tilting movements of the crystal 7 with the X-ray source 5. The implementation of such possibilities is within the capabilities of those of ordinary skill in the art.

The omni-directional adjustability of the X-ray source 5 can be implemented by any of a number of conventional ways. The crystal 7 can be tilted by the tilting arrangement 13 so that the angle of incidence $\Theta$ of the X-ray path 9 changes. In the illustration in the figure, the tilting motion of the crystal 7 occurs in one of the planes in the drawing plane. Due to a rigid spatial arrangement of the X-ray source 5 and the monochromator 1, the angle $\Theta$ can be changed only by tilting the crystal 7. However, in an alternative arrangement, the crystal 7 can be rigidly mounted in space within the monochromator 1, and the X-ray source 5 can be tilted relative to the monochromator 1. As previously described, in another variant the crystal 7 and the X-ray source 5 are always tilted simultaneously so that the ray path of the spectrally restricted radiation 11 remains spatially unchanged and thus the focus of the ray path does not shift.

Another possible adjustment of the crystal 7 is to fully remove the crystal 7 from the X-ray path 9 or to return it using a shifting device 15. By doing this, the influence of the crystal 7 changes so that Bragg reflection of the X-ray path 9 is quite eliminated. The X-rays in the X-ray path 9 then have the original energy spectrum determined by the X-ray source 5 and its operation parameters. The option of removing the crystal 7 allows operation either with spectrally restricted X-radiation or with unrestricted X-radiation depending on the type of the required image. In addition, removing or returning the crystal 7 to the X-ray path 9 changes the entire ray path, which can be compensated for in the above-described manner. The parameters defining the energy spectrum of the spectrally restricted X-radiation 11 are set in the control device 17. In accordance with the invention, these parameters include, besides the X-ray voltage and the X-ray current, the tilt angle of the crystal 7 and the positioning in or outside the X-ray path 9. The line 23 conducts the signals from the control device 17 that to control the movements of the ceiling stand 25 and positioning of the crystal 7 as well as, if necessary, of the X-ray source 5. Thus, the control device 17 controls the positioning device, i.e., the tilting arrangement 13, and the shifting device 15. Therefore, the control device 17 can coordinate the tilting movement of the X-ray source 5 with the tilting movement of the crystal 7 in the above-described way so that the beam path of the X-radiation 11 remains uncharged and its focus does not shift.

Selection of the angle of incidence Θ of the X-ray path 9 on the crystal 7, should be based on a voltage as high as possible, because the efficiency of an X-ray tube used as the X-ray source 5 increases with the square of the X-ray voltage. The utilization of Bragg reflection according to the invention makes it possible to produce X-radiation of relatively low energy levels with a simultaneous high efficiency of the X-ray source 5. In addition, the relatively high X-ray voltage reduces the blooming effect, which causes enlargement of the focal spot. In order to be able to utilize these advantageous effects enabled by the increased X-ray voltage, the incidence angle Θ is set so that the maximum value of the energy spectrum of the spectrally restricted X-radiation 11 is not greater than the 0.8-multiple of the maximum value of the energy spectrum of the X-ray 9.

Besides the maximum value of the energy spectrum in the reflected X-ray, Bragg reflection contains maxima of higher order as expressed by the factor k in the Bragg relation. In order to keep the influence of the refractions of higher order in the reflected X-ray small, the maximum value of the energy spectrum of the spectrally restricted X-radiation 11 is set to no less than the 0.34-multiple of the maximum value of the energy spectrum of the X-ray path 9. This guarantees especially that refraction from the $3^{rd}$ order on do not enter the spectrally restricted X-radiation 11.

Adherence to the described upper and lower limits can be automatically ensured using the control device 17. In addition, the control device 17 can automatically set the angle Θ so that after the definition of the X-ray voltage or a maximum value for the energy spectrum of the spectrally restricted X-radiation 11 or a factor between the maximum values of the energy spectrum of the X-ray path 9 and the spectrally restricted X-radiation 11, the operation of the X-ray device occurs with optimal efficiency, as low blooming effects as possible or with other parameters optimized. In this way, the control of the monochromator 1 and the X-ray source 5 is substantially automated thus utilizing the resulting advantages, which include no need for an operator to enter special parameters. Moreover, depending on the type of the required image to be produced, the control device 17 can remove the crystal 7 from the X-ray 9 or return it.

On the basis of the optical law of reflection, this invention can be used with advantage especially in applications using a fan ray, e.g., line scanners in CT apparatuses, and in applications that scan a whole area, e.g., angiography of extremities.

Although modifications and changes may be suggested by those skilled in the art, it is the intention of the inventors to embody within the patent warranted hereon all changes and modifications as reasonably and properly come within the scope of their contribution to the art.

We claim as our invention:

1. A monochromator for use with an X-ray radiator that emits X-rays having a spectral composition, said X-ray radiator having an operating voltage associated therewith, said monochromator comprising:

a crystal having a property of spectrally restricting X-rays interacting therewith to a spectral range having a spectral composition, said spectral range encompassing multiple energies and exceeding a spectral range provided by Bragg's relation from single crystal lattice;

a positioning device connected to said crystal to move said crystal relative to the X-rays emitted by said X-ray radiator to change said spectral composition of the X-rays; and a control device connected to said positioning device for automatically controlling said positioning device to control movement of said crystal dependent on said operating voltage.

2. A monochromator as claimed in claim 1 wherein said positioning device moves said crystal to alter an angle between at least a portion of said X-rays and said crystal.

3. A monochromator as claimed in claim 1 wherein said positioning device moves said crystal into and out of a path of said X-rays.

4. A monochromator as claimed in claim 1 wherein said spectral range comprises a restricted range energy spectrum with a maximum value, and wherein said control device sets said maximum value and controls said positioning device dependent on the maximum value that has been set.

5. A monochromator as claimed in claim 1 wherein said X-rays emitted by said X-ray radiator have an emitted energy spectrum with a first maximum value, and wherein said crystal spectrally restricts said X-rays emitted by said X-ray radiator to produce spectrally restricted energy spectrum with a second maximum value, and wherein said control device sets a factor between said first maximum value and said second maximum value and controls said positioning device dependent on said factor that has been set.

6. A monochromator as claimed in claim 5 wherein said control device sets said factor in a range between 0.3 and 0.8.

7. An X-ray device comprising: an X-ray radiator that emits X-rays having a spectral composition, said X-ray radiator having an operating voltage associated therewith; and a monochromator comprising a crystal having a property of spectrally restricting X-rays interacting therewith to a spectral range having a spectral composition, said spectral range encompassing multiple energies and exceeding a spectral range provided by Bragg's relation from single crystal lattice, a positioning device connected to said crystal to move said crystal relative to the X-rays emitted by said X-ray radiator to change said spectral composition of the X-rays, and a control device connected to said positioning device for automatically controlling said positioning device to control movement of said crystal dependent on said operating voltage.

8. An X-ray device as claimed in claim 7 wherein said positioning device moves said crystal to alter an angle between at least a portion of said X-rays and said crystal.

9. An X-ray device as claimed in claim 7 wherein said positioning device moves said crystal into and out of a path of said X-rays.

10. An X-ray device as claimed in claim 7 wherein said spectral range comprises a restricted range energy spectrum with a maximum value, and wherein said control device sets said maximum value and controls said positioning device dependent on the maximum value that has been set.

11. An X-ray device as claimed in claim 10 wherein said X-rays emitted by said X-ray radiator have an emitted energy spectrum with a first maximum value, and wherein said crystal spectrally restricts said X-rays emitted by said X-ray radiator to produce spectrally restricted X-rays having an energy spectrum with a second maximum value, and wherein said control device allows setting of a factor between said first maximum value and said second maximum value and controls said positioning device dependent on said factor that has been set.

12. An X-ray device as claimed in claim 11 wherein said control device sets said factor in a range between 0.3 and 0.8.

* * * * *